United States Patent [19]
Simkiss et al.

[11] Patent Number: 6,024,985
[45] Date of Patent: Feb. 15, 2000

[54] BONE MATERIALS

[75] Inventors: Kenneth Simkiss; Marina Gloria Taylor, both of Oxon, United Kingdom

[73] Assignee: University of Reading, Reading Oxon, United Kingdom

[21] Appl. No.: 08/373,252

[22] PCT Filed: Jul. 20, 1993

[86] PCT No.: PCT/GB93/01519

§ 371 Date: Apr. 5, 1995

§ 102(e) Date: Apr. 5, 1995

[87] PCT Pub. No.: WO94/02412

PCT Pub. Date: Feb. 3, 1994

[30] Foreign Application Priority Data

Jul. 20, 1992 [GB] United Kingdom ................... 9215356

[51] Int. Cl.$^7$ .......................... A61K 33/06; A61K 6/033; C01B 25/32; A61L 27/00
[52] U.S. Cl. .......................... 424/602; 424/601; 424/603; 424/604; 424/605; 424/606; 424/678; 424/681; 424/682; 424/683; 424/686; 424/692; 424/697; 424/57; 514/77; 514/81; 623/11; 623/16; 106/35
[58] Field of Search ...................................... 424/600, 601, 424/602, 603, 604–606, 678, 681–683, 686, 692, 697, 57; 514/77, 81; 623/11, 16; 106/35

[56] References Cited

U.S. PATENT DOCUMENTS

| Re. 33,211 | 5/1990 | Brown et al. | 423/308 |
|---|---|---|---|
| 2,041,473 | 5/1936 | Janota, Jr. | 424/57 |
| 4,113,500 | 9/1978 | Ebihara et al. | 423/308 |
| 4,684,673 | 8/1987 | Adachi | 523/116 |
| 4,917,702 | 4/1990 | Scheicher | 623/16 |
| 5,037,639 | 8/1991 | Tung | 424/57 |
| 5,522,893 | 6/1996 | Chow et al. | 623/11 |
| 5,650,176 | 7/1997 | Lee et al. | 424/602 |

FOREIGN PATENT DOCUMENTS 557314 11/1957 Belgium .
8807498 10/1988 WIPO .

OTHER PUBLICATIONS

Chemical Abstracts 110:87229r, Mar. 1989.
Eidelman, N. et al., "The effect of pyrophosphate concentrations on calcium phosphate growth on well–crystallized octacalcium phosphate and hydroxyapatite seed crystals," J. Cryst. Growth, vol. 108(1–2), pp. 385–393, 1991.
Chemical Abstracts 114:154095, 1991.
Eidelman, N. et al., "Selective inhibition of crystal growth on octacalcium phosphate and nonstoichiometric hydroxyapatite by pyrophosphate at physiological concentration," J. Cryst. Growth, vol. 113(3–4), pp. 643–652, 1991.
Chemical Abstracts 115:252917, 1991.
Thomas, S.A., "Effects of some ions on the conversion of amorphous calcium phosphate to calcium hydroxyapatite in aqueous medium," Bull. Chem. Soc. Ethiop., vol. 5(1), pp. 11–20, 1991.
Chemical Abstracts 116:224953, 1992.
Nancollas, G.H. et al., "The precipitation of calcium phosphate in the presence in the presence of magnesium," Croat. Chem. Acta, vol. 48(4), pp. 431–438, 1976.
Chemical Abstracts 86:81796, 1977.

*Primary Examiner*—John Pak
*Attorney, Agent, or Firm*—Pillsbury Madison & Sutro LLP

[57] ABSTRACT

The invention provides a synthetic bone precursor material comprising amorphous calcium phosphate and a constituent that inhibits the crystallisation of calcium hydroxyapatite to amorphous calcium phosphate. The synthetic bone precursor may comprise a material of formula $Ca_xMg_yPO_4$ wherein Mg acts as an inhibitor for crystallisation. Other crystallisation inhibitors such as pyrophosphate may be present. The inhibitor is capable of dissolving in physiological saline. Loss of inhibitor from the precursor allows crystallisation of hydroxyapatite. The invention relates to use of a synthetic bone precursor to form bone in vivo, by a transformation of the amorphous precursor material to crystalline hydroxyapatite bone material by the leaching action on inhibitory ions body fluids. it is envisaged that the material will be useful in facilitating bone repair, inducing bone formation or assisting in the attachment of prostheses.

2 Claims, 1 Drawing Sheet

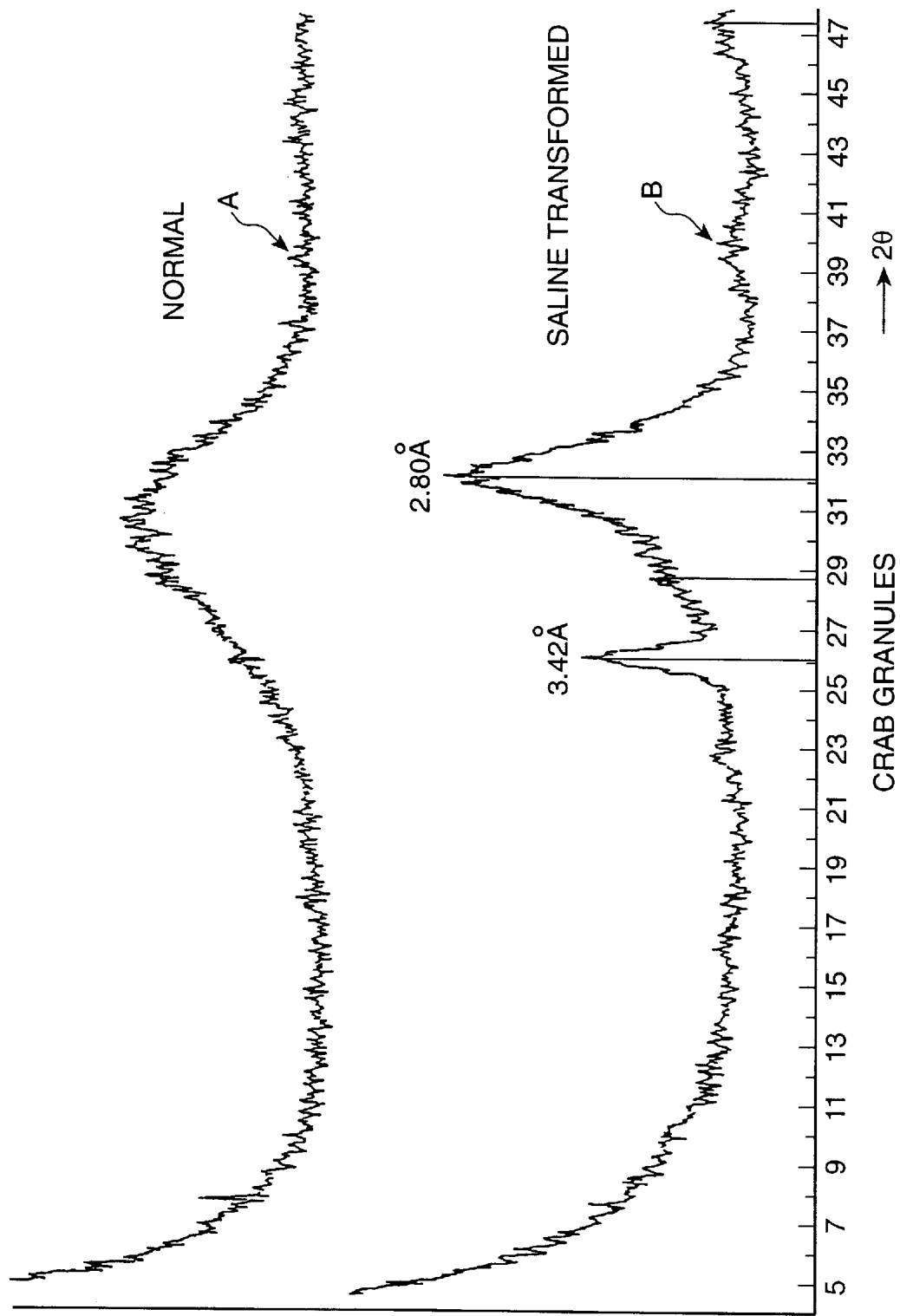

BONE MATERIALS

This application is a 371 of PCT/GB93/01519, filed on Jul. 20, 1993.

BACKGROUND OF THE INVENTION

The present invention relates to materials useful in producing bone mineral or similar material; to their preparation; and to their use.

Bone has organic and inorganic constituents. Most of the strength is due to the inorganic material, of which the major part is crystalline calcium phosphate, particularly hydroxyapatite, $Ca_5(OH)(PO_4)_3$. This crystalline material is strong, stable and essentially insoluble.

SUMMARY OF THE INVENTION

We have now found certain substantially amorphous materials that can be transformed under controlled conditions into crystalline bone material which may be of natural type or similar strong, stable material. Thus in one aspect the invention concerns use of certain precursor materials in the manufacture of a composition for use in a therapeutic technique in which bone is built up in vivo by transformation of the composition to produce bone material.

The precursor materials contain, as principal inorganic constituents, amorphous non-stoichiometric compounds containing calcium and phosphate ions. The phosphate ions may be mainly or wholly derived from phosphoric acid ($H_3PO_4$); they may include a proportion of ions derived from pyrophosphoric acid ($H_4P_2O_7$). Generally the compounds contain magnesium ions.

The precursor materials may be essentially inorganic, particularly when made synthetically. Alternatively they may include organic components. These can be deliberately included in synthetic materials, or be naturally present in naturally-derived materials.

Generally, the number of moles of magnesium Der mole of calcium is in the range 0.001 to 1; for example 0.01 to 0.40 and preferably 0.1 to 0.16

Material may be synthesised by bringing together calcium ions, magnesium ions, and phosphate ions in a buffer solution under conditions-such that a material of desired composition is precipitated. Other components can be included in the reaction solution if desired.

Naturally-derived materials can be prepared from naturally-occurring deposits of amorphous calcium/magnesium/phosphate minerals. Suitable deposits occur in the soft tissue of many invertebrates (see. e.g. G. L. Becker et al., *J. Cell Biology*, (1974), 61, 316–326 at page 322 and references cited therein), notably the intracellular granules from the digestive glands of various invertebrates, particularly crabs and snails e.c. as described in K. Simkiss et al, *j.Inora.Biochem*, (1990), 39, 17–23, and G. L. Becker et al, op cit. Thus as described by Simkiss et al, granules can be extracted from *C.maenas* by homogenisation of the digestive gland and centrifugation in water to afford a clean white product. This product consists largely of inorganic phosphate, with the metal ions being mainly calcium but with some magnesium (the molar ratio being about 9: 1). The phosphate includes ions derived from phosphoric and pyrophosphoric acids, primarily from phosphoric acid. There are also organic components, mainly adenosine phosphates. (In general, such granule-derived material may contain significant amounts of nucleosides and glycoproteins.)

Materials may be prepared or selected which contain different proportions of one or more crystallisation inhibitor components such as magnesium and/or pyrophosphate and/or organic components, in order to control the rate of conversion to bone material under predetermined (generally physiological) conditions. At its simplest, a precursor material is an amorphous composition which contains calcium and phosphate ions as primary constituents together with inhibitor components (notably magnesium and/or pyrochosphate ions) which inhibit its transformation to a crystalline form (generally based on hydroxyapatite). In use the precursor material gradually loses inhibitor components (in particularly, magnesium ions) by leaching action to ambient body fluids, and undergoes transformation into crystalline hydroxyapatite. Where pyrophosphate ions are used as crystallisation inhibitor the molar ratio of $P_2O_7$ to $PO_4$ is in the range 0.001 to 0.2, preferably 0.01 to 0.1. Other inhibitor components which could be used in the invention are citrate ions and/or acrylate ions.

In vivo, the precursor material is applied to a site where bone growth is required. The inhibitors will gradually be lost to body fluid, leading to gradual transformation to bone mineral.

Because the lixiviated mineral is a biologically compatible product it is unlikely to produce any allergic effects. Furthermore the transformation of amorphous material into bone mineral is slow, e.g. taking days, so that it is likely to integrate into normal healing processes. The bone mineral that is formed is believed to be compatible with collagen mineralisation which would make it particularly useful for assisting in bone repair. It is envisaged that the material will be useful in facilitating bone repair, inducing bone formation or assisting in the attachment of prostheses.

BRIEF DESCRIPTION OF THE DRAWING

FIG. 1 shows in trace A, an X-ray diffraction pattern of naturally-derived material prepared as specified in Example (1) below, and shows in trace B, an X-ray diffraction pattern of the same material after having been placed in physiological saline solution, inhibitor ions leached, and the sample isolated, washed and dried.

DESCRIPTION OF THE PREFERRED EMBODIMENTS

Some examples will now be described in more detail with reference to the accompanying drawing in which: FIG. 1 shows X-ray diffraction data for amorphous material and crystalline material.

EXAMPLES (1) Precursor Materials: Naturally Derived

Material was isolated from *C.maenas* and characterised as described in Simkiss et al, op.cit, the content of which is incorporated herein by reference.

(2) Precursor Materials: Synthetic

Material was prepared by techniques adapted from Termine, J. D. et al, *Arch. Biochem.Biphys.*, (1970), 140, 307–317 and 318–325, the content of which is incorporated herein by reference.

Calcium chloride solutions were made up in buffer (Tris HCl) to maintain the pH at about 7.4. Magnesium chloride was added to these solutions to produce a range of magnesium concentrations, the Mg: Ca mole ratio ranging from 1:1 to 0.01:1. A buffered phosphate solution (based on phosphoric acid) was added. The total concentrations were selected to approximate to 'natural' conditions: ion strength ca 0.15 (and pH ca 7.4). The solutions were stirred and the resulting precipitates were collected by centrifugation, followed by washing and drying at 60° C. The products were characterised by elemental analysis, IR spectroscopy and X-ray diffraction.

Transformation

FIG. 1 shows in trace A, an X-ray diffraction pattern of naturally-derived material prepared as specified at (1). A sample of the material was place, in physiological saline solution. The inhibitor ions will leach from the material. After many hours the sample was isolated, washed and dried and its X-ray diffraction pattern was determined again. This is trace B. It can be seen that there is clear evidence of ordering. That is, the material is no longer amorphous. The peaks representing d-spacings of crystalline hydroxyapatite (3.42 Å and 2.80 Å) are indicated.

Similar experiments were carried out with the synthetic samples prepared as specified at (2). It was found that the time taken to effect transformation varied with the concentration of magnesium in the sample. Samples in which some phosphate was substituted by pyrophosphate showed a similar variation in transformation time with pyrohospate concentration.

The rationale behind this reaction probably involves the following:
(i) Because the minerals are. amorphous they are more soluble than an equivalent crystal. They therefore start to dissolve.
(ii) As the minerals dissolve they tend to lose their high Mg content to the saline (in vivo, to the body fluids). This removes the inhibition to the nucleation of hydroxyapatite.
(iii) Bone mineral, which is less soluble than the amorphous deposit, now begins to form.
(iv) It is thought that initial bone deposits normally occur in gap regions of the organic collagen fibres. The crystals of bone in these collagen gaps are generally smaller than normal, probably because they contain magnesium ions. The bone crystals induced by the amorphous deposits may be of a similar type depending upon how fast the magnesium is lost.
(v) Because the bone mineral that has formed from these amorphous deposits is similar to normal bone it should integrate into the normal bone structures of the body and even be capable of being remodelled in vivo. In this it differs fundamentally from artificial adhesives.

It is possible to provide a wide range of materials based on amorphous $Ca_xMG_yPO_4$, with different x:y ratios. These will have different solubilities and rates of transformation into bone mineral. This will influence their speed of cementing and the properties of the mineral induced. Thus it is possible to produce a series of simple amorphous materials which
(i) transform into bone mineral at predetermined rates (possibly with varying adhesion properties) when exposed to the body fluids
(ii) produce bone minerals of different physical properties (e.g. crystallinity)
(iii) integrate into normal bone structures
(iv) are capable of being remodelled in the body and
(v) may act as a booster mechanism for normal bone repair.

Such substances are of value in providing an interface to assist the attachment of protheses, promoting normal bone repair and replacing normal mineral in damaged bones or even teeth (and the term "bone material" as used herein is to be understood to cover synthetic tooth material).

The amorphous compositions of the invention could also be included in a matrix containing other materials: for example they could be integrated in a matrix with a biologically active moeity to provide an "active composite".

Furthermore, according to this invention it is possible to mix several amorphous calcium phosphate materials chosen to have different rates of transformation so as to provide for a series of transformations (either overlapping in time or sequential). Transformation time can be controlled by choice of inhibitor (i.e. one or several ions which may be the same or different for each amorphous calcium phosphate constituent of the mixture) and choice of inhibitor concentration and/or solubility.

An important aspect of the invention resides in the biomedical uses which may be made of the materials. A slow transformation with a varying range of the inhibiting ions (e.g. magnesium of pyrophosphate) encourages natural bone formation and repair mechanisms.

A mixture of fast-setting and slow-setting compositions of the invention will encourage vascularisation of an adhesive material such as a poly methyl methacrylate cement and made such mixtures suitable for coating the contact area of implanted bone prostheses.

When manipulated into pre-formed shapes, mixtures of fast and slow-setting materials may be used in spinal surgery as bone-grafting materials and bone filling materials for dealing with the collapse of intervertebral discs. No artificial material has yet been found suitable for this application which has had to resort to the use of donor bone material from the pelvis of the same patient.

We claim:

1. A method in which synthetic bone material is formed in viva which comprises:
   positioning an amorphous precursor in the body at the point where the formation of bone is desired, said precursor consisting essentially of a solid mixture of:
   a) at least one amorphous calcium phosphate constituent, with the exception of tetra calcium phosphate $(Ca_4(PO_4)_2)O)$, and;
   b) at least one of magnesium ion and pyrophosphate ion constituent which acts as an inhibitor for crystallisation of hydroxyapatite $(Ca_5(OH)(PO_4)_3$ from amorphous calcium phosphate until the solid mixture is placed in a body where bone growth is required and comes in contact with body fluids,
   which inhibitor is capable of dissolving in physiological saline and is capable of leaching from the precursor to cause crystallisation of hydroxyapatite therefrom; and
   transforming the amorphous precursor into crystalline bone material by the effect of the leaching action of ambient body fluids on inhibitor b.

2. A method of treatment which results in the formation of synthetic bone material in vivo, said method comprising applying an effective amount of an amorphous precursor to the body of a human or animal patient at the point where bone material is to be formed, said precursor consisting essentially of a solid mixture of:
   a) at least one amorphous calcium phosphate constituent, with the exception of tetra calcium phosphate $(Ca_4(PO_4)_2)O)$, and;
   b) at least one of magnesium ion and pyrophosphate ion constituent which acts as an inhibitor for crystallisation of hydroxyapatite $(Ca_5(OH)(PO_4)_3$ from growth is required and comes in contact with body fluids,
   which inhibitor is capable of dissolving in physiological saline and is capable of leaching from the precursor to cause crystallisation of hydroxyapatite therefrom; and
   treating said human or animal patient by transforming the amorphous precursor into crystalline bone material by the effect of the leaching action of ambient body fluids on inhibitor b.

* * * * *